United States Patent

Schultz et al.

[11] Patent Number: 5,625,903
[45] Date of Patent: May 6, 1997

[54] HEADBAND WITH ADJUSTABLE SPEAKER SUPPORTING MEANS

[76] Inventors: Michael A. Schultz, 172 Hemingway Dr., Rochester, N.Y. 14620; Gavin McAuley, 170 Clovercrest Dr., Rochester, N.Y. 14618

[21] Appl. No.: 607,218

[22] Filed: Feb. 26, 1996

[51] Int. Cl.⁶ .................................. H04R 5/02; A42C 5/00
[52] U.S. Cl. .......................... 2/209; 2/209.13; 2/DIG. 11; 2/452
[58] Field of Search .............................. 2/209, 209.13, 2/DIG. 11, 423, 422, 181, 172, 452; 455/100, 351; 381/25, 187, 188

[56] References Cited

U.S. PATENT DOCUMENTS

| | | | |
|---|---|---|---|
| 4,654,898 | 4/1987 | Ishikawa | 2/209 |
| 4,683,587 | 7/1987 | Silverman | 2/426 |
| 4,776,044 | 10/1988 | Makins | 2/209.13 |
| 4,864,619 | 9/1989 | Spates | 381/187 |
| 5,038,412 | 8/1991 | Cionni | 2/DIG. 11 |
| 5,164,987 | 11/1992 | Raven | 381/187 |
| 5,201,856 | 4/1993 | Edwards | 2/209 |
| 5,257,420 | 11/1993 | Byrne, Jr. | 2/209 |
| 5,303,426 | 4/1994 | Jones | 2/209.13 |
| 5,329,592 | 7/1994 | Altman | 2/DIG. 11 |
| 5,438,698 | 8/1995 | Burton et al. | 2/209.13 |

*Primary Examiner*—Amy B. Vanatta

[57] ABSTRACT

The headband unit includes two enlarged fabric pockets disposed to overlie and cover the ears of the person wearing the unit. Each pocket is formed between two layers of fabric and contains an audio speaker support in the form of a strip of flexible plastic secured around its edges to the layer of fabric that engages the ear of the person wearing the unit, and having therein a plurality of spaced openings or slots each of which is adapted to receive and removably support an audio speaker in any of a plurality of different positions in the associated pocket so as to be registrable selectively with the ear of the person wearing the unit.

8 Claims, 2 Drawing Sheets

HEADBAND WITH ADJUSTABLE SPEAKER SUPPORTING MEANS

BACKGROUND OF THE INVENTION

This invention relates to headbands of the type which are worn by skiers and joggers, and more particularly to headbands having means for removably and adjustably supporting therein two audio signal speakers which are adapted to register with the ears of the wearer.

With the rise in popularity of leisure sports such as skiing and jogging, a variety of rather sophisticated headbands have been developed for the comfort and convenience of such athletes. As an added attraction many such headbands, or headgear generally, have been supplemented with stereo headsets having audio earphones or speakers which are mounted in or attached to the headbands to provide music or communication to the wearer while skiing or jogging. A variety of U.S. patents, such as for example U.S. Pat. Nos. 4,864,619, 5,421,037, 5,164,987, 4,683,587, 4,538,034, 4,776,044, 5,257,420, 4,654,898 and 5,265,165 show various combinations of headband or spectacle frame devices with associated audio signal speakers or headphones.

A major problem with each of the above-noted prior art devices, however, is that no satisfactory provision has been made for adjustably supporting the associated audio speakers on the headband, or the like so that the speakers can easily be placed in positions in which they will be held in exact registry with the ears of the wearer. In the above-noted U.S. Pat. No. 4,538,034, for example, the illustrated earphones or speakers are attached to bracket members each of which can be inserted beneath a person's headband in such manner that a lateral projection on the upper end of the member overlies the headband to support an earphone thereon. In U.S. Pat. No. 5,257,420 the headphones are mounted in earmuffs, each of which has therein one slot for accommodating the speaker associated with a respective ear. Again, there are no means for adjusting the speakers into any one of a number of different positions with respect to each ear.

It is an object of this invention, therefore, to provide a novel headband which can be utilized by athletes, such as joggers or skiers, in combination with a pair of audio signal speakers which can be adjustably mounted on the headband in any of a plurality of different positions with respect to the ears of the person wearing the headband.

A more specific object of this invention is to provide for an improved headband of the type described which has incorporated therein a pair of audio speaker or headphone supporting elements that are mounted on the headband to register generally with the ears of the associated wearer, and each of which elements has therein a plurality of spaced sockets or openings for accommodating an audio speaker, so that each speaker can be placed to register exactly with the adjacent ear of the person wearing the headband.

Other objects of this invention will be apparent hereinafter from the specification and from the recital of the appended claims, particularly when read in conjunction with the accompanying drawings.

SUMMARY OF THE INVENTION

In one embodiment a generally U-shaped headband is made from an elongate piece of fabric disposed to be folded intermediate its longitudinal side edges over the elastic band that is used to secure a ski goggle device to the head of a skier. Opposite sides of folded fabric extend over and enclose opposite sides of the elastic band; and the longitudinal side edges of the fabric are releasably secured together by VELCRO tape, or the like. Ajdacent opposite ends thereof the folded headband has slightly enlarged portions thereof disposed to cover the ears of the person wearing the goggle device, and each of which portions forms a pocket containing a speaker support in the form of a flexible plastic strip of rectangular configuration. Each strip is secured around its edges to the inner side of the folded fabric engaging the head of the wearer, and has therethrough three, spaced, elongate slots each of which is generally bowling-pin-shaped, and the lower ends of which register with small openings in the inner side of the folded fabric.

In use, before the fabric is folded over the elastic goggle band, each of two audio speakers is removably mounted in one of the slots in one of the two speaker supports, and so that the output end of the speaker registers with one of the small openings in the inner side of the folded layer. The fabric headband can then be mounted on the elastic gogle band, and if the spearers do not register properly with the wearer's ears, the ends of the fabric can be reopened and the speakers may be positioned in others of the slots in the supports until they reach the desired, adjusted positions.

In the second embodiment the headband is made from two elongate, endless fabric layers the marginal edges of which are secured together to form an endless headband. As in the first embodiment, two spearer supports are mounted in enlarged portions of the headband adjustably to support speakers as in the first embodiment. In this second embodiment, however, the outer layer of the headband has therein two elongate slots, each of which register with the lower ends of all three slots in a respective speaker support so that the speakers can be adjusted from slot to slot by inserting one's fingers through one of the slots in the outer layer.

THE DRAWINGS

DETAILED DESCRIPTION OF THE PREFERRED EMBODIMENTS

Figure 1:
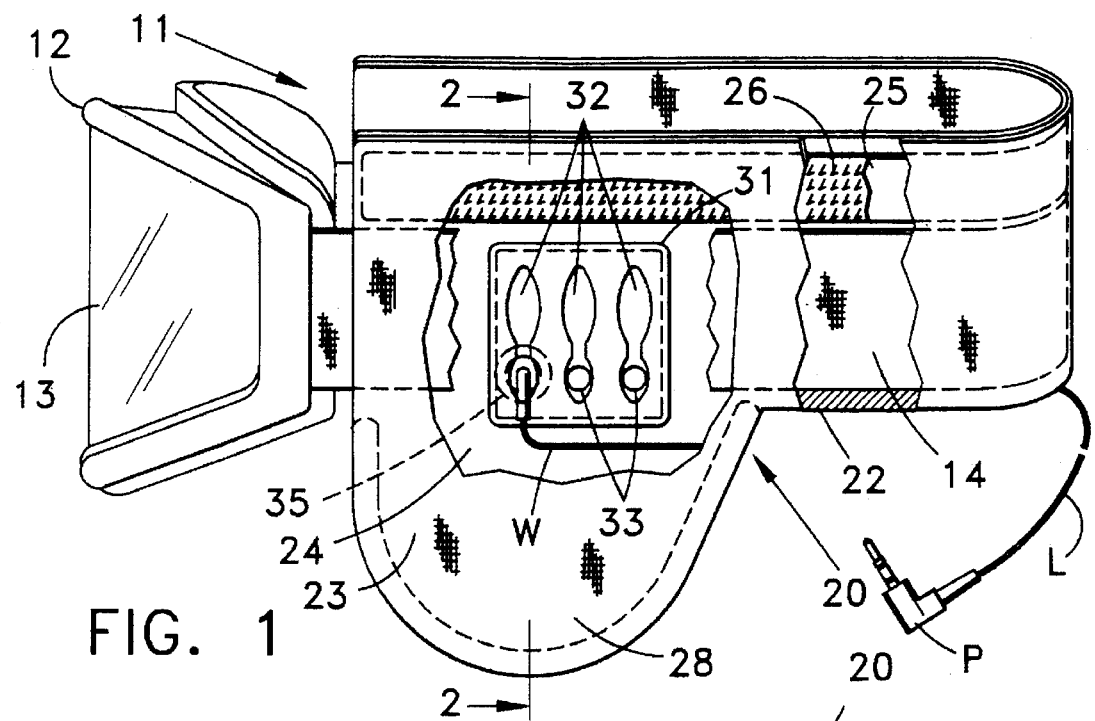
FIG. 1 is a perspective view approximating a side elevation of an improved headband made according to one embodiment of this invention, the headband being illustrated as it appears when it has been releasably mounted on the elastic strap of a conventional ski goggles unit, and with a portion of the outer layer of the headband being broken away for purposes of illustration.
Figure 2:
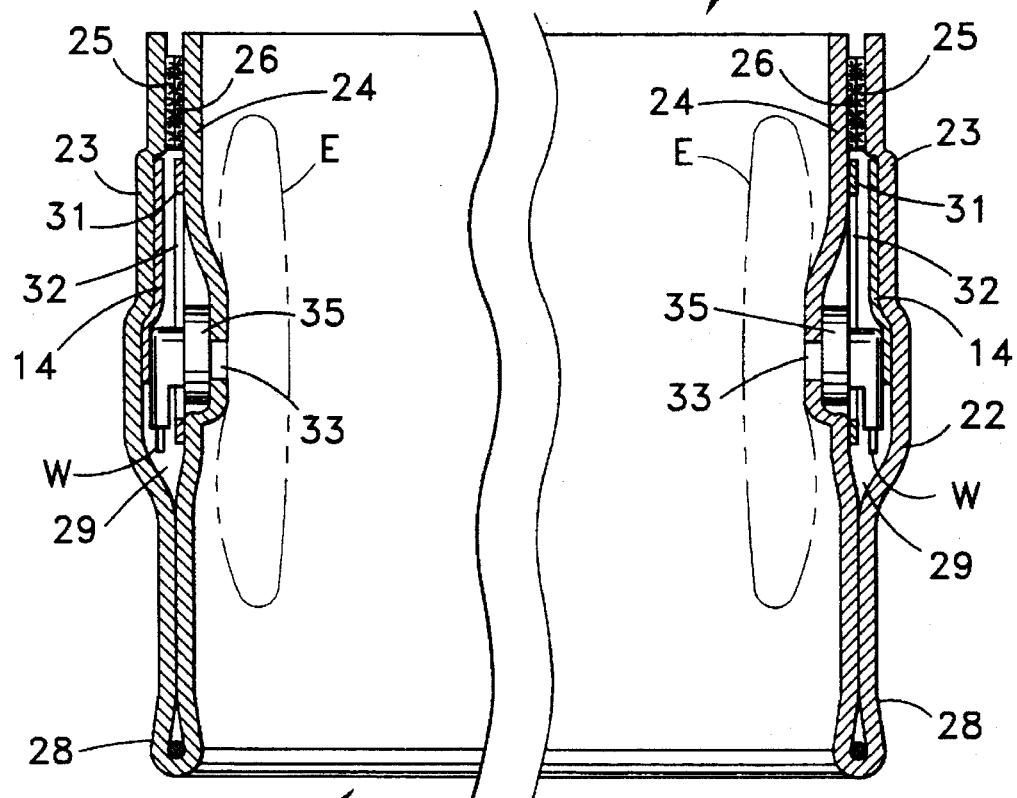
FIG. 2 is a fragmentary sectional view taken generally along the line 2—2 in FIG. 1 looking in the direction of the arrows.

Referring now to the drawings by numerals of reference, and first to FIGS. 1 and 2, 11 denotes generally a conventional ski goggle device comprising a flexible, semi-rigid frame 12 containing the usual tinted transparency 13. Opposite ends of the goggle frame 12 are attached to opposite ends of an elastic band 14 of conventional design, and which is disposed to extend resiliently around the back of the head of the person wearing the goggle frame.

The numeral 20 denotes generally a novel headband comprising an elongate piece of fabric folded intermediate its longitudinal side edges so that opposite sides 23 and 24 thereof extend upwardly over opposite sides of the strap 14. Cooperating VELCRO hook and loop strips 25 and 26, which are secured to and extend along the inside surfaces of the upper edges of sides 23 and 24, respectively, of the now-folded fabric 22 secure the upper edges of the sides 23 and 24 releasably together. The folded fabric 22, which now appears generally U-shaped in configuration, thus encloses the strap 14 between the outer side 23 and the inner side 24 of fabric 22. At opposite ends thereof the now-folded fabric 22 has slightly enlarged portions 28, which curve downwardly as shown in FIG. 1 so that the inner sides 24 thereof will cover the ears E (shown in phantom by broken lines in FIG. 2) of the person wearing the headband 20. These enlarged end portions 28 of the fabric 22 form pockets 29 for accommodating audio speakers, as noted hereinafter.

Mounted in each pocket 29 on the side 24 of the folded fabric 22 is a speaker supporting member 31. Each member 31 comprises a generally rectangularly-shaped plastic strip, which is stitched or otherwise secured around its marginal edges to the inside surface of side 24 of the folded fabric. Between opposite ends thereof each member 31 has formed therethrough three elongate, equispaced slots or openings 32, the longitudinal axes of which extend at right angles to the length of the folded fabric 22 and the strap 14 over which the fabric is folded. Each slot 32 is larger at its upper end and smaller at its lower end, thus having a configuration somewhat similar to an inverted bowling pin. Adjacent each end of the folded fabric the inner side 24 thereof has therein three rather small, spaced, circular openings 33, each of which registers coaxially with the lower end of one of the slots 32 in the adjacent member 31.

In use, before fabric 22 is folded over the strap 14, each of two audio speakers 35 is inserted through one of the slots 32 in a support 31 in one of the chambers 29, and is positioned adjacent the lower end of the slot so that the output end of the speaker registers with one of the circular openings 33 in the side 24 of fabric 22. The wire leads W, which project from the backs of the speakers 35, then pass to the rear of the headband 20, where they enter a lead L that extends out of the headband 20 and is connected at its opposite end to a conventional plug P, which is adapted to be connected in a known manner to a signal source (not illustrated), such as a small radio or the like. The fabric 22 can then be folded about the strap 14 in a manner similar to that noted above; and if the speakers 35 do not register properly with the ears of the person wearing the headband 20, the opposite sides of the folded fabric 22 at opposite ends thereof can be opened to permit the wearer to shift the speakers 35 into another of the two remaining slots 32 until such time that the speakers properly register with the ears of the wearer.

One of the advantages of this construction is that the support members 31 not only permit adjustment of the speakers into different longitudinal positions in the headband 20, but also the slots or openings 32 are shaped in such manner that they secure the speakers 35 against accidental shifting when the headband is in use. Also, the openings 33, which are disposed to register with the speakers 35, permit the tips of the speakers to be inserted through registering openings 33 and into the ears of the wearer, depending of course upon the configuration of the output end of respective speaker 35.

Figure 3:
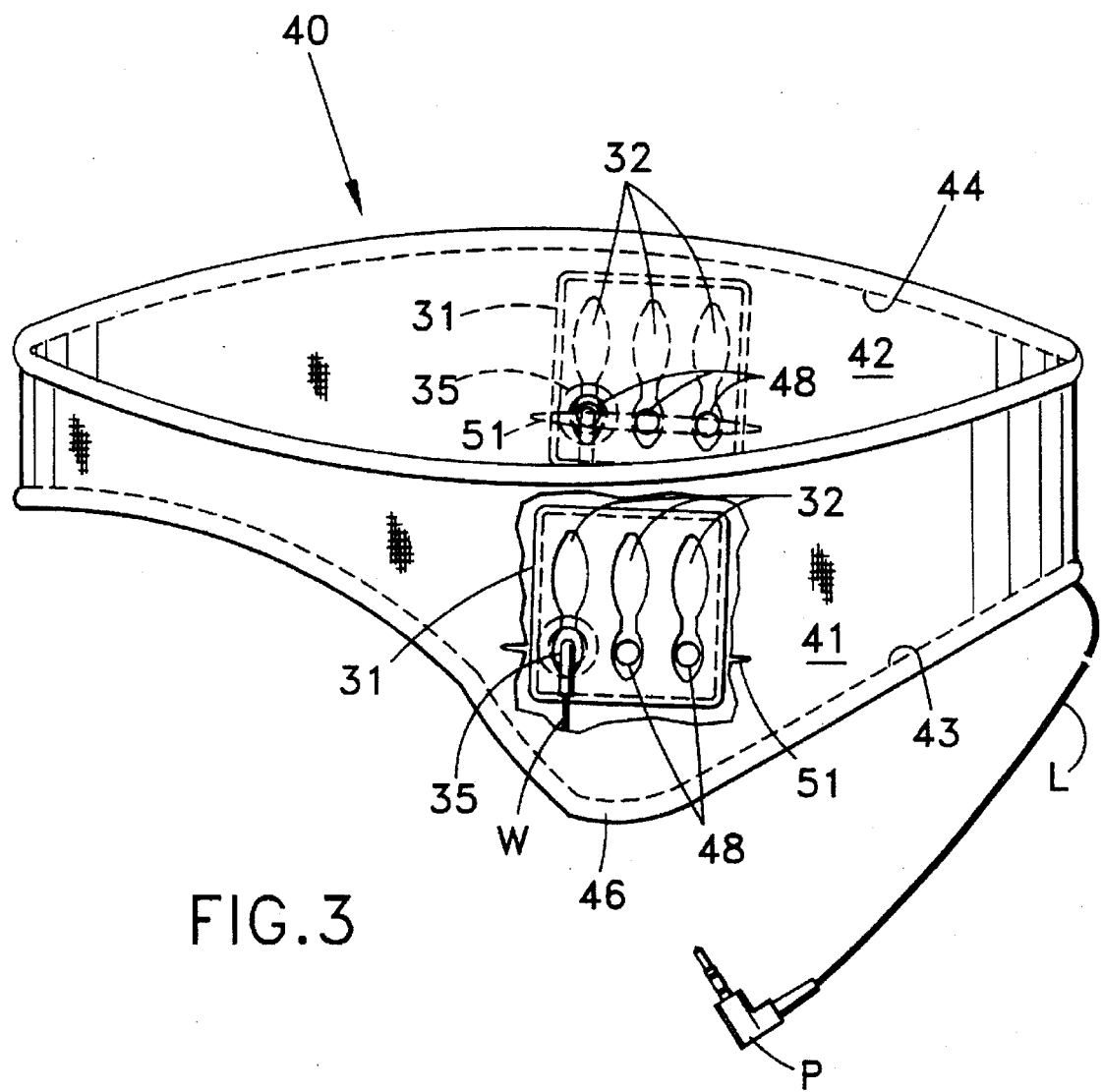
FIG. 3 is a perspective, side elevational view of the modified form of this novel headband, and with a portion of the outer layer thereof being broken away for purposes of illustration.

Referring now to the embodiment shown in FIG. 3, wherein like numerals are employed to denote elements similar to those described in connection with the first embodiment, 40 denotes generally a modified headband which, unlike the headband 20, forms a complete or endless headband. A band of this type is designed completely to surround the head of a person wearing the headband, such as for example a jogger who has no particular need for using the headband in conjunction with ski goggles of the type shown in the first embodiment. Headband 40 comprises two endless, like layers 41 and 42 of fabric which, in the embodiment illustrated are stitched or otherwise secured together adjacent their marginal edges along stitch lines 43 and 44, respectively. As in the case of the first embodiment, the layers 41 and 42 have enlarged portions 46 thereof which curve or extend downwardly adjacent the back of the headband in order to cover the ears of the person wearing the headband.

Mounted in the enlarged portions 46 of the headband 40 between its layers 41 and 42 to register, generally, with the ears of the person are two speaker supports 31, which are similar to those employed in the first embodiment. Each such support 31 has therein the three, spaced slots 32 the lower ends of which register with circular openings 48 that are formed in each enlarged section of the inner layer 42. Openings 48 function in the same manner as the openings 33 in the first embodiment. Unlike the outer layer or side 23 of the fabric shown in the first embodiment, however, the outer layer 41 of the headband 40 has formed therein two, elongate slits or openings 51, each of which is formed in an enlarged portion of the layer 41 to extend transversely of the slots 32 in the adjacent support 31, and to register intermediate its ends with such slots adjacent the openings 48.

In use, the lead L carrying the two wires W for associated audio speakers, is inserted through an opening in the rear end of the headband 40, and the two speakers 35 attached to its wires W are removably mounted in respectively different ones of the supports 31. As shown in FIG. 3, for example, one speaker 35 is removably mounted in the slot 32 formed in the left end of the support 31 shown by full lines in this figure, and the other speaker 35 is removably mounted in the corresponding or registering slot 32 formed in the other support 31. In order to effect the proper mounting of the speakers 35 in the supports 32, the elongate slots 51 in the outer layer 41 of fabric permit a person to insert his or her fingers through each opening 51 in order to grasp and insert a speaker 35 in one of the support slots 32; and if necessary, to remove and insert a respective speaker into another of the three slots in a respective support 31 until such time that the speakers 35 register properly with the ears of the person wearing the headband 40.

From the foregoing, it will be apparent that the present invention provides relatively simple and inexpensive means for very accurately and adjustably mounting audio speakers in headbands of the type discussed above. The speaker supports 31 are flexible, light, and inexpensive; and they can be provided with speaker support openings 32 which can be shaped to conform to standard speakers of the type which are employed with conventional radios or recorders that are adapted to be carried on the body of a person wearing the headband. The advantage of headbands of the type described is that they enable a considerable reduction in the number of differently sized headbands that must be produced in order to accommodate differently shaped or sized heads. Substantially one size headband, for example, can be suitable for use for almost all occasions, since the person wearing the headband can readily adjust the position of each associated speaker 35 simply by positioning it in one of the several receptacles or slots provided by the associated support 31.

While this invention has been illustrated and described in connection with specially shaped openings slots in the supports 31, it will be apparent to one skilled in the art that those shapes can be changed without departing from the nature of this invention. Also, of course, conventional means other than VELCRO fasteners can be employed to secure together the registering edges of the sides 23 and 24 of the fabric 22. Moreover, while this invention has been illustrated and described in detail in connection with only certain embodiments thereof, it will be apparent that it is capable of still further modification, and that this application is intended to cover any such modifications as may fall within the scope of one skilled in the art, or the appended claims.

We claim:

1. In a headband unit of the type disposed removably to be mounted on a person's head, and having thereon two enlarged fabric pockets disposed to register with and cover the ears of the person wearing the headband unit, and each of which pockets is formed between two layers of fabric, one of which layers is disposed to engage and cover an ear of the person wearing the headband unit, improved means for adjustably mounting audio speakers in said pockets, comprising a pair of flexible speaker supports each of which is mounted in a different one of said pockets, and each of which supports is secured around its marginal edges to said one layer of fabric of a respective pocket, and each of said supports having therethrough a plurality of elongate, spaced openings, and each of said openings being shaped to receive and removably to secure on the associated support an audio speaker with the output thereof facing an ear of the person wearing the headband unit.

2. In a headband unit as defined in claim 1, wherein said one layer of fabric of each of said pockets has therethrough a plurality of openings each of which registers with one of said openings in the associated support.

3. In a headband unit as defined in claim 2, wherein the openings in each of said one layers of fabric are smaller than the openings in said supports.

4. In a headband unit as defined in claim 3, wherein each of said elongate openings in said supports is larger at one end therof than the other end thereof.

5. In a headband unit as defined in claim 1, wherein said two enlarged fabric pockets form portions of a fabric band disposed to surround the head of a person wearing the unit.

6. In a headband unit as defined in claim 5, wherein each of the other of said two layers of fabric forming a respective pocket has therein an elongate opening extending transversely of and registering intermediate its end with said plurality of elongate openings in said support that is mounted in the associated pocket.

7. In a headband unit as defined in claim 1, including a ski goggle frame attached at opposite ends thereof to opposite ends of an elastic strap disposed to engage behind a person's head removably to secure the ski goggle frame over the eyes of the person wearing the unit, said two layers of fabric being folded intermediate the longitudinal side edges thereof to extend over and enclose opposite sides of said elastic strap with said pockets located adjacent said opposite ends of said frame, and means releasably securing the longitudinal side edges of said fabric together to retain the folded fabric on said strap.

8. In a headband unit as defined in claim 7, wherein each of said supports is interposed between said elastic strap and said one layer of said fabric to which the respective support is secured.

* * * * *